United States Patent [19]
Boudjema

[11] Patent Number: 6,059,807
[45] Date of Patent: May 9, 2000

[54] DEVICE FOR IMPLANTING SMALL-DIAMETER CAPILLARY GRAFTS

[75] Inventor: Pascal J. Boudjema, Paris, France

[73] Assignee: Apex Medical Products, LLC, Las Vegas, Nev.

[21] Appl. No.: 09/266,268

[22] Filed: Mar. 11, 1999

[30] Foreign Application Priority Data

Mar. 17, 1998 [FR] France .................................. 98-03240

[51] Int. Cl.$^7$ .................................................. A61B 17/34
[52] U.S. Cl. ........................................... 606/187; 606/185
[58] Field of Search ................................... 606/187, 185, 606/184, 115, 123, 1, 606, 133; 623/15

[56] References Cited

U.S. PATENT DOCUMENTS

| | | | |
|---|---|---|---|
| 4,160,453 | 7/1979 | Miller ...................................... | 128/330 |
| 4,221,212 | 9/1980 | Miller ...................................... | 606/187 |
| 4,378,019 | 3/1983 | Yamada .................................. | 128/330 |
| 4,479,291 | 10/1984 | Yamada .................................. | 128/330 |
| 4,751,927 | 6/1988 | Yamada .................................. | 128/330 |
| 5,417,683 | 5/1995 | Shiao ...................................... | 606/1 |
| 5,578,054 | 11/1996 | Arnold .................................... | 606/185 |
| 5,611,810 | 3/1997 | Arnold et al. .......................... | 606/185 |
| 5,693,064 | 12/1997 | Arnold .................................... | 606/184 |
| 5,782,843 | 7/1998 | Aasberg .................................. | 606/133 |
| 5,782,851 | 7/1998 | Rassman ................................. | 636/167 |
| 5,817,120 | 10/1998 | Rassman ................................. | 606/187 |
| 5,827,297 | 10/1998 | Boudjema ............................... | 606/133 |
| 5,989,279 | 11/1999 | Rassman ................................. | 606/187 |

FOREIGN PATENT DOCUMENTS

| | | |
|---|---|---|
| 92 12105 | 4/1994 | France . |
| 2715823 | 8/1995 | France . |
| 95 09824 | 2/1997 | France . |
| 2744624 | 8/1997 | France . |
| 42 43 641 | 9/1994 | Germany . |
| WO 95/28896 | 11/1995 | WIPO . |

*Primary Examiner*—Michael Buiz
*Assistant Examiner*—Kevin Truong
*Attorney, Agent, or Firm*—Fitzpatrick, Cella, Harper & Scinto

[57] ABSTRACT

A device for implanting a small-diameter capillary graft into the scalp, comprising a hollow needle pierced by a through-bore having a smaller diameter than the graft and suitable for gripping, by its end, one end of the said graft through the needle. The needle is mounted so as to slide in a cylindrical sheath between a first position, in which the needle is retracted inside the sheath, and a second position for gripping and for inserting the graft into the scalp, in which the needle projects beyond the end of the sheath. The needle is actuated between the first and second positions, preferably by application and release of a vacuum to an enclosure which is defined by a cylindrical tube and which is closed on a first side by the sheath and on a second side by a plug fastened to a distal end of the needle. A communication port is formed in the needle communicating with the enclosure, so as to allow vacuum in the enclosure to facilitate gripping of the capillary graft by vacuum, and an orifice is provided in a wall of the cylindrical tube so as to allow a surgeon rapidly to apply and release vacuum in the enclosure.

26 Claims, 2 Drawing Sheets

DEVICE FOR IMPLANTING SMALL-DIAMETER CAPILLARY GRAFTS

BACKGROUND OF THE INVENTION

1. Field Of The Invention

The present invention relates to a device for implanting small-diameter capillary grafts into the scalp, comprising a hollow needle for gripping, at the end of it, a graft by suction and a device for rapidly withdrawing the needle.

One particularly important, but not exclusive, application of the invention is in the field of the surgical treatment of baldness by grafting natural hair, and more particularly in the field of micrografting.

2. Description Of The Related Art

The surgical treatment of baldness by capillary transplantation, called the graft technique, consists in transplanting into the same individual part of the roots of his hair located in the (still hairy) crown from the crown to the bald areas.

The grafts are cylindrical skin fragments usually obtained either by making a circular cut in the skin using a rotating cylindrical tool, directly from the scalp, or by cutting, on a hard surface using a bistoury blade, a strip of scalp removed beforehand from the crown, into many small cylindrical skin fragments each containing one to a few hair roots. Once removed, these small-sized grafts (approximately 1 mm in diameter and 5 mm in length), called micrografts, are generally gripped by means of microgrippers and then manually reimplanted, one by one, in respective receding sites prepared beforehand in the scalp.

Capillary graft implantation devices are already known.

For example, there is a suction implantation device (FR 92 12105) which comprises a hollow needle into which the entire graft is sucked up and then pushed out by a piston in its receding site.

Such a device has drawbacks. This is because it relies on complex connections of nozzles, requires perfect pre-sizing of the grafts to the internal diameter of the hollow needle, in order to prevent the needle from becoming obstructed, and does not allow the surgeon to see the depth of implantation of the graft, most particularly when the graft is inserted into a small incision in the scalp.

Manual implantation grippers are also known (FR 95 09824) which comprise two graft-gripping arms with retractable semicylindrical jaws.

Such grippers also have drawbacks. This is because they require perfect pre-sizing of the grafts to the internal diameter of the jaws, making it necessary for the graft to be oriented and positioned axially between the two jaws before it is implanted.

Consequently, the already existing devices do not allow grafts of variable size to be easily implanted and are limited in their applications. In addition, using them requires tiresome operations and manipulations, lengthening operating times.

SUMMARY OF THE INVENTION

The present invention addresses the above-mentioned drawbacks by providing a device which meets practical requirements better than those previously known, especially since the device allows micrografts of variable size to be implanted rapidly, inexpensively and in a simple and easily implementable manner.

The device further is easy to sterilize. The low manufacturing cost also makes single use possible, allowing the device, in certain embodiments, to be thrown away after use.

In one aspect, the invention provides a device for implanting a small-diameter capillary graft into the scalp. The device includes a hollow needle pierced by a throughbore having a smaller diameter than the graft and suitable for gripping one end of the graft by suction through the needle, the needle being mounted so as to slide in a cylindrical sheath between a first position in which the needle is retracted, and a second position in which the needle is projected beyond the tip of the sheath for gripping a graft by suction and for inserting the graft into the scalp. The device further includes means for actuating the needle between the first and second positions, and means for rapidly returning said needle to the first position after releasing the graft.

Rapid return should be understood to mean almost instantaneous return, for example in about one tenth of a second.

In preferred embodiments, the means for actuating the needle comprises a cylindrical tube defining an enclosure closed on one side of the sheath and blocked off on the other side by a plug fastened to one end of the needle, the plug being suitable for sliding snugly inside the tube between two stop positions corresponding to the first and second positions of the needle, the means for actuating the needle additionally comprising means for creating a vacuum in the enclosure and means for letting air into the enclosure, the first and second positions corresponding respectively to the letting of air into and to the creation of a vacuum in the enclosure. The plug may be removable.

Creation of a vacuum should be understood to mean creation of a normal vacuum (for example 0.2 bar absolute) obtained by a vacuum pump in a manner that is conventional in a surgical context.

In other preferred embodiments, the wall of the needle has an opening for communication between the bore of the needle and the enclosure, so that the letting of air into and the creation of a vacuum in the enclosure on the one hand, in order to actuate the needle, and the suction and release of the graft on the other hand, take place simultaneously by the same suction and the same letting-in of air.

In still other preferred embodiments, the means for rapidly returning the needle to the first position comprises a coil spring suitable for being compressed when the enclosure is under vacuum and suitable, when the vacuum is broken by letting air in, for pushing back the plug away from that end of the tube which lies on the sheath side. The means for letting air into the enclosure comprises an orifice drilled in the cylindrical wall of the tube, suitable for being blocked off by a finger of the surgeon operating the device. The surgeon may thus actuate the needle by simply blocking off the orifice with his finger or by exposing the orifice, while the vacuum pump continues to operate without interruption.

It is preferred for the gripping end of the needle to include at least two teeth with a softened tip curved over towards the inside of the needle. Such an arrangement provides complementary mechanical attachment of the graft to the end of the needle. The gripping end of the needle may provide two teeth of unequal length in the axial direction of the needle, or the gripping end of the needle may provide three teeth, or the end of the needle may be adapted for cutting. Such an arrangement allows the graft to be put into position ordinarily without the need to bore out the scalp beforehand in order to form the site for receiving the graft.

It is further preferred for the gripping end of the needle to be removable, that is, removably fixed to the body of the needle. The length of the projecting end of the needle in the second position is preferably adjustable with respect to the tip of the sheath.

It will be understood that the present device may be easily manufactured from plastic and consequently is advantageously disposable, in order to avoid any risk of subsequent contamination.

However, it can also be cleaned and reused, if desired, after sterilization. In such situations, it is ordinarily preferable to fabricate the device from easily sterilizable materials such as surgical stainless steel.

The present invention will be more clearly understood on reading the following description of a preferred embodiment thereof given by way of a non-limiting example.

DETAILED DESCRIPTION OF THE PREFERRED EMBODIMENT

Figure 1:
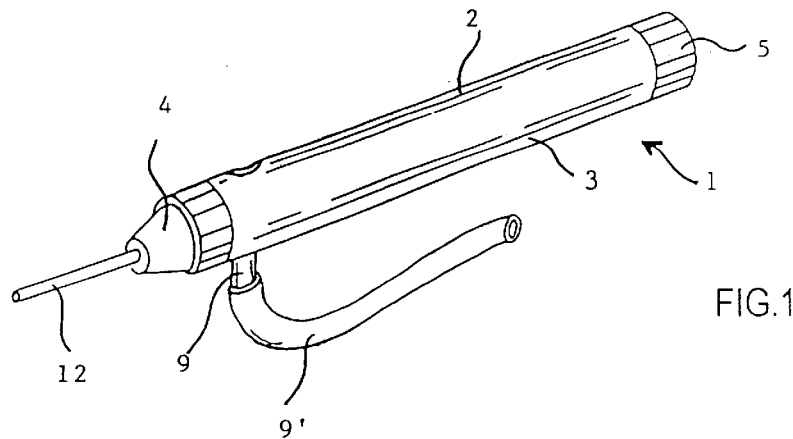
FIG. 1 is a perspective view showing a first embodiment of a device according to the invention.
Figure 2:
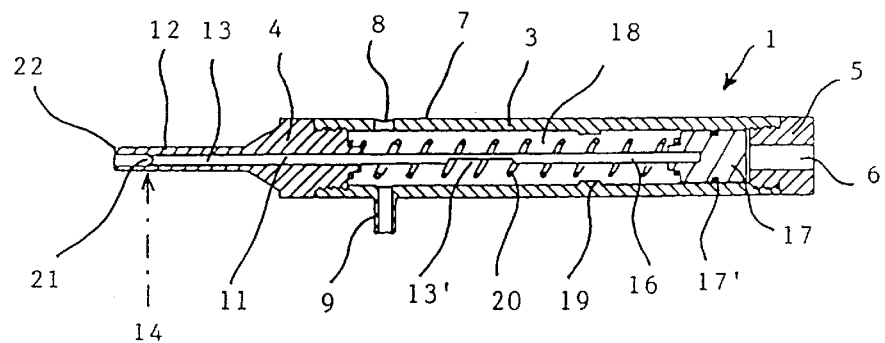
FIG. 2 is a longitudinal sectional view of the device of FIG. 1 in the first position, at rest, with the needle retracted.
Figure 3:
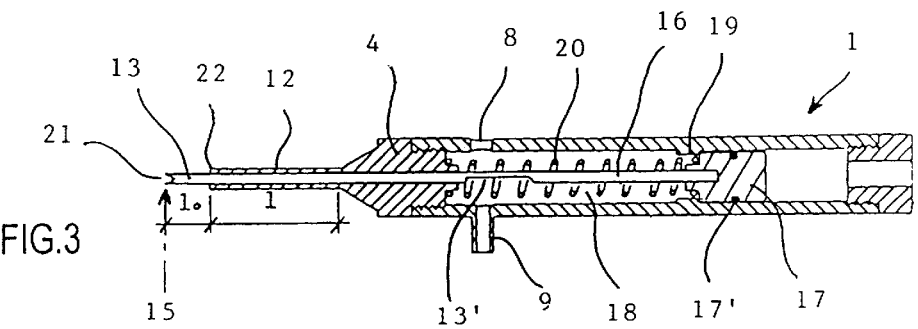
FIG. 3 is a longitudinal sectional view of the device of FIG. 1 in the second, suction position, with the needle projecting.

FIGS. 1, 2 and 3 show a device (1) for implanting capillary grafts which comprises a hand piece comprising a hollow body (2) formed by a cylindrical tube (3) terminated at the front part by a tip piece (4) and closed at the rear part by a removable plug (5) pierced by a throughbore. Tip piece (4) and plug (5) are removably fixed to cylindrical tube (3) by complementary screw threads.

The cylindrical wall (7) of the hollow body (2) has, in its upper part as viewed in FIG. 2, and arranged closely adjacent tip piece (4), a venting orifice (8) and, in its lower part, a tap or nozzle (9) for removable connection to a source of vacuum (0.2 bar absolute) via a hose (9').

The tip piece (4) is pierced by an axial throughbore (11) extended to the front by a cylindrical sheath (12) approximately 20 mm in length and 1 mm in internal diameter, inside which a loosely fitting hollow implantation needle (13) slides freely.

The hollow needle (13) is pierced by a bore having a smaller diameter than the smallest of the cut grafts, for example having a bore diameter of 0.5 mm.

The hollow needle moves with a predefined travel between a first, rest position (14) (cf. FIG. 2) and a second, suction position (15) (cf. FIG. 3).

The distal end (16) of the needle, i.e. the end internal to the tube (3), is fixed removably to a plug (17) suitable for sliding in the tube in an air sealed manner with respect to the cylindrical wall of the tube, by virtue of an O-ring (17').

Tip piece (4) and plug (17) define, with the internal wall of the tube, a chamber or enclosure (18) whose volume varies between the first position (14), in which the plug (17) butts against the removable plug (5), and the second position (15), in which the plug (17) butts against an internal ring (19) projecting from the internal wall of the tube.

The venting orifice (8) and the tap (9) are located in such a way that they are always connected to the enclosure (18), regardless of whether plug (17) is in the first or second position.

A compression coil spring (20) placed within the tube (3) allows the plug (17) to move back rearwards against the plug (5) and therefore allows the needle (13) to be withdrawn when the orifice (8) is exposed, and vacuum is released.

The hollow implantation needle (13), the dimensions of which are, for example, about 1 mm in external diameter, 0.5 mm or 0.6 mm in internal diameter and 80 mm in length, has, in its middle part, an oblong orifice (13') allowing the creation of a vacuum in the internal bore of the needle and therefore in its end (21) when the vacuum is maintained in the cylindrical enclosure (18), as illustrated in FIG. 3.

The length l of the sheath (12) is designed to allow the needle to be fully retracted in the first position, the end (21) of the needle then being completely withdrawn inside the sheath, and to allow the end (21) to project outwards, away from the tip (22) of the sheath, in the second position.

The length $l_o$ of the projecting part may, for example, be adjusted by screwing/unscrewing the sheath or the tip piece with respect to the body of the device. The length $l_o$ is calculated, for example, so as to correspond to the depth of the implantation site. In addition, the length $l_o$ may be adjusted by changing the placement of plug (17) on distal end (16) of needle (13).

Figure 4:
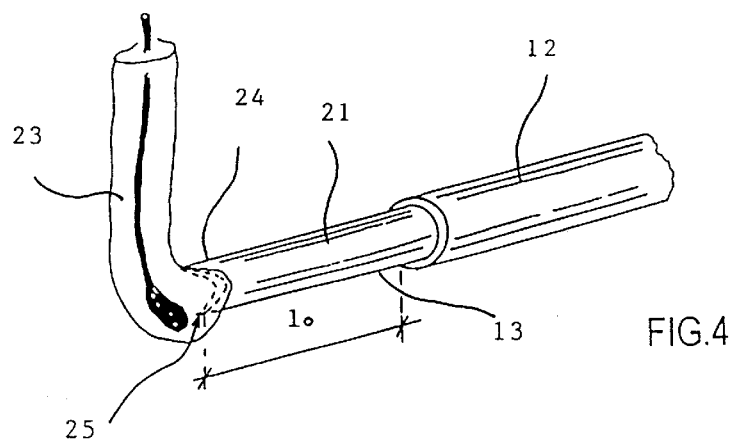
FIG. 4 is a perspective view on a large scale of the end of the needle, illustrating the gripping of the graft by suction.

FIG. 4 is a perspective view on a large scale illustrating the way the graft (23) is fixed on the end of the needle (13), in the suction mode.

It may be seen that the hollow needle (13) projecting from the tip of the sheath (12) has a suction orifice (24) shaped so as to allow the graft (23) to be attached by suction and held firmly but not traumatizingly by small teeth (25).

The diameter of the orifice (24) is smaller than the diameter of the graft (23) so as to prevent the latter from being sucked up into the needle (13).

Figures 5, 6, 7, 8, 9, 10, 11:
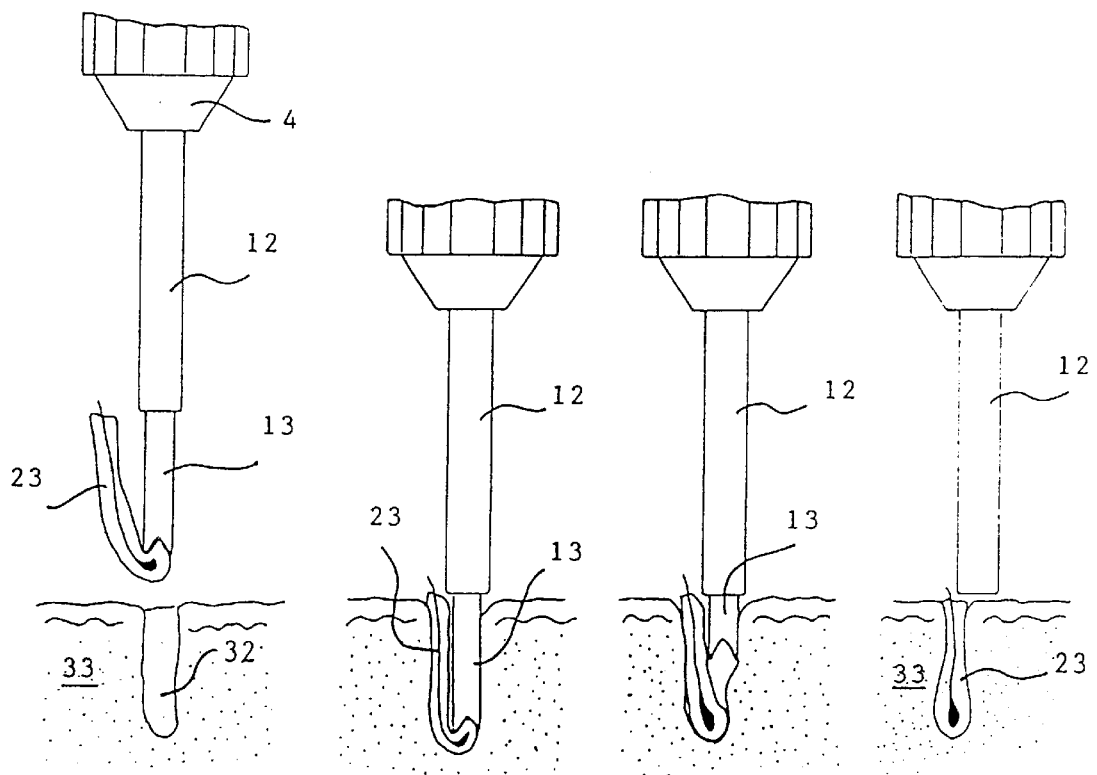
FIGS. 5, 6 and 7 are side views showing various alternative forms of the end of the needle forming part of a device according to the invention.
FIGS. 8, 9, 10 and 11 are vertical views on a large scale illustrating the method of using the device according to the invention.

FIGS. 5, 6 and 7 are partial side views illustrating various alternative forms of the end of the needle (13).

In FIG. 5, the front suction orifice (24) of the needle (13) has small hook-type teeth (26), approximately 0.5 mm in length, with a slightly softened point (27) curved over towards the inside so that the teeth do not catch on the skin when inserting the graft into the scalp.

FIG. 6 illustrates an end (28) with two asymmetrical teeth (29) and (30) in which the forward-most, bevelled and cutting, tooth (29) is intended to penetrate directly into the skin.

The suction orifice (24) is located slightly set back from the cutting point in such a way that the graft is conjointly inserted into the incision in the skin thus created by the point.

FIG. 7 shows an end with three identical and angularly distributed teeth (31) which have a curved tip and are approximately in the shape of an equilateral triangle.

FIGS. 8, 9, 10 and 11 are vertical views on a large scale illustrating the method of using the device according to the invention.

Preparatory to surgery, the surgeon sets the depth of implantation $l_o$. The implantation depth may be set by screwing/unscrewing the sheath (12) or tip piece (4) with respect to the body of the device, or by changing placement of plug (17) on distal end (16) of needle (13), as described above.

In use, the surgeon closes venting orifice (8) with his finger so as to create a vacuum in chamber (18) and cause needle (13) to extend from its rest position to its suction position. The surgeon then attracts a follicle end of a graft to the needle tip where the graft is held in place by suction.

FIG. 8 illustrates the way in which the graft (23), fixed at its base by suction to the end of the needle (13), is presented to its receiving site (32) made previously in the scalp (33).

FIG. 9 illustrates the actual insertion of the graft (23) which is slipped into the scalp while still being held on the end of the implantation needle (13) by suction. The insertion of graft (23) to its proper insertion depth is facilitated by the extension of needle (13) to length $l_o$ which corresponds to the depth of implantation.

FIG. 10 illustrates the almost instantaneous retraction of the needle (13) into the sheath (12), a fraction of a second after breaking the vacuum inside the needle (13), caused by exposing the orifice (8) for letting air into the enclosure and into the internal bore of the needle by the surgeon's finger.

This operation of letting air in has two effects: the graft (23) on the end of the needle (13) is released and the needle (13) is retracted into the sheath (12).

FIG. 11 illustrates the perfect positioning of the graft (23) within the scalp (33), the implantation needle (13) being fully retracted inside the sheath (12).

Although incision (32) has been shown as pre-formed prior to implantation, it is possible to form the incision (32) concurrently with implantation if the tip design includes a cutting blade, such as the tip illustrated in FIG. 6.

The cylindrical body (2) of the device of the invention more particularly described here may be made of metal, such as treated aluminum or a stainless steel, or else a sterilizable rigid plastic, such as polycarbonate.

Its dimensions may, for example, be 8 cm in length and its external diameter 12 mm, the front sheath (12) being made of stainless steel and the plug (17) of metal or plastic.

The implantation needle (13) may be made of stainless steel. It is easily interchangeable.

The vacuum source is of the air-pump type. It must generate a sufficiently high vacuum (approximately 800 mBar to allow), on the one hand, the piston formed by the needle (13) and the plug (17) to move forwards in the cylinder and, on the other hand, to keep the graft (23) held on the end (13) of the needle by suction.

The way in which the device according to the invention more particularly described here is used will now be described.

The device (1) is connected to a vacuum source, for example a continuously operating vacuum pump, by means of the hose (9').

The device is then held in the manner of a pen, leaving the air suction orifice (8) exposed.

The implantation needle (13) is in the retracted position inside the sheath (12).

Obstructing the air suction orifice (8) using a finger (index finger) causes a sudden vacuum to be created in the cylindrical chamber (18), this having the effect of pushing the plug (17) forwards and the implantation needle (13) forwards from the sheath (12) by length $l_o$ which is typically around 6 mm.

The end orifice (24) of the needle (13) thus becomes a sucking orifice, and is brought until just in contact with the base of a graft (23) removed beforehand, thus having the effect of pressing it against the teeth of the end of the needle by suction.

Since the air suction orifice (8) is still kept blocked off by the finger, the instrument is moved to the receiving site and the graft, still adhering to the needle, is then inserted with the latter into its receiving site (32).

Once the graft (23) has been positioned in its site, exposing the air suction orifice (8) by lifting the finger breaks the vacuum, by air being drawn into the cylindrical chamber (18) and, at the same time, at the front orifice (24) of the end of the needle (13), releasing the graft from the implantation needle (13) which is almost instantaneously withdrawn from the receiving site, the needle being attracted by the plug which is itself pushed back by the spring (20) into its initial rest position, thus leaving the graft perfectly well positioned in the scalp.

The air suction orifice (8) is then blocked off by the finger, the instrument being ready to catch hold of the next graft.

As goes without saying and as, moreover, results from the foregoing, the invention is not limited to the embodiment of the invention more particularly described. On the contrary, it encompasses any variant thereof and especially those in which the means for actuating the needle are different, for example pneumatic or electrical means.

What is claimed is:

1. A device for implanting a small-diameter capillary graft into a scalp, comprising:

a hollow needle having a throughbore whose diameter is smaller than that of said capillary graft, said hollow needle having a gripping end for gripping one end of said capillary graft by suction through the needle;

a cylindrical sheath mounting said needle so as to slide between a first position in which said needle is retracted and a second position in which said gripping end of said needle is extended beyond a tip end of said cylindrical sheath for gripping by suction and inserting said capillary graft into the scalp;

means for actuating said needle from said first position to said second position; and means for rapidly returning said needle from said second position to said first position after releasing said capillary graft.

2. A device according to claim 1, wherein said means for actuating said needle comprises:

a cylindrical tube defining an enclosure closed on a first side by the sheath and blocked off on an opposing side by a plug fastened to a distal end of said needle, said plug being suitable for sliding snugly inside of said tube between two stop positions corresponding to said first and said second positions of said needle;

means for creating a vacuum in said enclosure; and means for letting air into said enclosure, wherein said first position and said second position of said needle correspond respectively to the letting of air into the enclosure and to the creation of a vacuum in the enclosure.

3. A device according to claim 2, further comprising a communication path through a wall of said needle for communication between said throughbore of said needle and said enclosure, wherein, letting of air into said enclosure actuates said needle from said second position and simultaneously releases said capillary graft from said gripping end of said needle, and creation of a vacuum in said enclosure actuates said needle from said first position to said second position and simultaneously grips said capillary graft by suction at said gripping end of said needle.

4. A device according to claim 3, wherein the means for rapidly returning the needle to said first position from said second position comprises a coil spring tensioned when said enclosure is under vacuum, and when said vacuum is broken by letting air into said enclosure, said coil spring translates said plug and said needle fastened to said plug away from the end of the tube enclosed by the sheath.

5. A device according to claim 2, wherein the means for letting air into said enclosure comprises an orifice through a wall of said cylindrical tube suitable for being blocked off by a finger of a person operating the device.

6. A device according to claim 2, wherein said plug is adjustably fastened on said needle.

7. A device according to claim 1, wherein said gripping end of said needle comprises at least two teeth having a softened tip curved over towards said needle bore.

8. A device according to claim 1, wherein said gripping end of said needle comprises two teeth of unequal length in an axial direction of said needle.

9. A device according to claim 1, wherein said gripping end of said needle has three teeth.

10. A device according to claim 1, wherein said gripping end of said needle is for cutting.

11. A device according to claim 1, wherein said gripping end of said needle is removably fixed to a body of said needle.

12. A device according to claim 1, wherein an amount of needle projection beyond said tip end of said sheath in said second position is adjustable with respect to said tip end of said sheath.

13. A device according to claim 1, wherein the diameter of the throughbore of said hollow needle is substantially about 0.5 mm.

14. A device for implanting a small-diameter capillary graft into a scalp, comprising:
   a hollow needle having a throughbore, said hollow needle having a gripping end for gripping one end of said capillary graft by suction through the needle;
   a cylindrical tube terminating in a cylindrical sheath for slidably receiving said needle, said cylindrical tube defining an enclosure closed on a first side by the sheath and closed on an opposing side by a plug slidably received inside said cylindrical tube and fastened to a distal end of said needle, said cylindrical tube including means for applying a vacuum to said enclosure and means for opening and closing said enclosure to ambience;
   said hollow needle further including a communication path through a wall thereof for communication between said throughbore and said enclosure, said hollow needle being mounted in said cylindrical sheath so as to slide between a first position in which said needle is retracted within said cylindrical sheath and a second position in which said gripping end of said needle is extended beyond a tip end of said cylindrical sheath; and
   means for biasing said hollow needle toward said retracted position.

15. A device according to claim 14, wherein said plug is adjustably fastened on said needle.

16. A device according to claim 14, wherein said gripping end of said needle comprises at least two teeth having a softened tip curved over towards said needle bore.

17. A device according to claim 14, wherein said gripping end of said needle comprises two teeth of unequal length in an axial direction of said needle.

18. A device according to claim 14, wherein said gripping end of said needle has three teeth.

19. A device according to claim 14, wherein said gripping end of said needle is for cutting.

20. A device according to claim 14, wherein said gripping end of said needle is removably fixed to a body of said needle.

21. A device according to claim 14, wherein an amount of needle projection beyond said tip end of said sheath in said second position is adjustable with respect to said tip end of said sheath.

22. A device according to claim 14, wherein the diameter of the throughbore of said hollow needle is substantially about 0.5 mm.

23. A method for implanting a small-diameter capillary graft into a scalp, said method being performed with a device that includes a hollow needle having a throughbore, said hollow needle having a gripping end for gripping one end of said capillary graft by suction through the needle;
   a cylindrical tube terminating in a cylindrical sheath for slidably receiving said needle, said cylindrical tube defining an enclosure closed on a first side by the sheath and closed on an opposing side by a plug slidably received inside said cylindrical tube and fastened to a distal end of said needle, said cylindrical tube including means for applying a vacuum to said enclosure and means for opening and closing said enclosure to ambience;
   said hollow needle further including a communication path through a wall thereof for communication between said throughbore and said enclosure, said hollow needle being mounted in said cylindrical sheath so as to slide between a first position in which said needle is retracted within said cylindrical sheath and a second position in which said gripping end of said needle is extended beyond a tip end of said cylindrical sheath; and
   means for biasing said hollow needle toward said retracted position,
   said method comprising the steps of:
      closing off said means for opening the enclosure to ambience, so as to create a vacuum in the enclosure and actuate the needle from the first position to the second position, and so as to cause suction at the gripping end of the needle by communication of the vacuum through the communication path;
      gripping the capillary graft at the gripping end of the needle by said suction;
      implanting the small-diameter capillary graft into an incision in the scalp; and
      opening said means for opening the enclosure to ambience, so as to release vacuum in said enclosure, thereby releasing the capillary graft from the gripping end of the needle and allowing said means for biasing to retract said needle to the first position.

24. A method according to claim 23, wherein said means for opening the enclosure to ambience is comprised by an orifice, and wherein said step of closing off comprises the step of blocking the orifice with a finger tip.

25. A method according to claim 23, wherein said gripping end of said needle includes a cutting tip, and further comprising the step of forming an incision with said cutting tip concurrently with said step of implanting the capillary graft.

26. A method according to claim 23, further comprising the step of adjusting implantation depth by adjusting by which said needle extends from said cylindrical sheath in said second position.

* * * * *